(12) United States Patent
Roiniotis

(10) Patent No.: US 8,399,853 B2
(45) Date of Patent: Mar. 19, 2013

(54) UV STERILIZER

(75) Inventor: Nick Roiniotis, Bulleen (AU)

(73) Assignee: A.P.E. Enterprises Pty Ltd, Bulleen (AU)

( * ) Notice: Subject to any disclaimer, the term of this patent is extended or adjusted under 35 U.S.C. 154(b) by 428 days.

(21) Appl. No.: 12/600,440

(22) PCT Filed: May 14, 2008

(86) PCT No.: PCT/AU2008/000679
§ 371 (c)(1),
(2), (4) Date: Jan. 14, 2010

(87) PCT Pub. No.: WO2008/141363
PCT Pub. Date: Nov. 27, 2008

(65) Prior Publication Data
US 2010/0143188 A1      Jun. 10, 2010

(30) Foreign Application Priority Data

May 17, 2007   (AU) ................................ 2007902648

(51) Int. Cl.
*G01N 23/00* (2006.01)
*H01J 37/20* (2006.01)

(52) U.S. Cl. ............. 250/455.11; 250/453.1; 250/504.1; 250/461.1; 422/22; 422/24

(58) Field of Classification Search ............. 250/455.11, 250/453.1, 504 R, 461.1; 422/22, 24
See application file for complete search history.

(56) References Cited

U.S. PATENT DOCUMENTS 6,461,568 B1 * 10/2002 Eckhardt ........................ 422/24
7,202,484 B1 * 4/2007 Tantillo .................... 250/455.11

FOREIGN PATENT DOCUMENTS

WO         2004031706 A1       4/2004

* cited by examiner

*Primary Examiner* — Jack Berman
*Assistant Examiner* — Meenakshi Sahu
(74) *Attorney, Agent, or Firm* — Sughrue Mion, PLLC

(57) ABSTRACT

A UV sterilizer for oral appliances comprising, (a) a base including a UV source, (b) a lid, and (c) an appliance holder intermediate the lid and the base, the appliance holder being adapted to hold the oral appliance adjacent the UV source, wherein pressure exerted on the appliance holder can activate the UV source.

11 Claims, 5 Drawing Sheets

UV STERILIZER

CROSS REFERENCE TO RELATED APPLICATION

This application is a National Stage of International Application No. PCT/AU2008/000679 filed May 14, 2008, claiming priority based on Australian Patent Application No. 2007902648, filed May 17, 2007, the contents of all of which are incorporated herein by reference in their entirety.

FIELD OF THE INVENTION

The invention relates to a UV steriliser. In particular the present invention relates to a UV steriliser for oral appliances.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

While the following specification is directed to sterilisation of pacifiers or teats, the skilled person will appreciate that the invention is not so limited but includes other types of oral appliances such as mouthguards, orthodontic retainers and dentures.

Ultraviolet (UV) light refers to all electromagnetic radiation with wavelengths in the range of 10 to 400 nanometres, or frequencies from 7.5E14 to 3E16 Hz. UV light is often used for sterilisation both in large scale industrial applications and in smaller, commercial and domestic applications. It is particularly effective for control of microorganisms such as bacteria, moulds, fungi and viruses which are readily made airborne and settle on exposed surfaces where they rapidly multiply.

In order to inactivate or kill microorganisms, UV light must actually strike the microorganism. UV energy penetrates the outer cell membrane, passes through the cell body, and disrupts its DNA, preventing reproduction of the microorganism. Depending on its wavelength, UV light may also interact with oxygen and other species to create ozone, a radical molecule that attacks and destroys microorganisms, and in the process breaks down to harmless oxygen.

In domestic applications UV has been used in applications such as toothbrush sterilisation. For example the Orasafe™ toothbrush sterilizer uses a UV/ozone lamp to eliminate up to 99.99% of germs from toothbrushes, which helps to address problems such as tooth decay, gum disease and halitosis. The Orasafe™ device comprises a rectangular, hinged lid box into which a toothbrush is placed with the bristles adjacent a UV lamp. The UV lamp is activated by closing the hinged lid. The UV lamp emits a specific range of UV radiation which kills the microorganisms or damages their DNA so that they cannot reproduce.

UV has also been used to sterilise pacifiers and teats. A pacifier (as it is called in the USA) is also known as a 'dummy' in the UK, New Zealand and Australia or a 'soother' in Canada and Ireland and consists of a rubber or plastic nipple that is given to an infant or young child to suck upon. A teat is a rubber or plastic nipples that are attached to bottles for feeding babies.

Korean company Esenscia provides the 'Pacifier Steriliser™' product which comprises a small essentially rectangular container having a hinged door which encloses a space in which pacifier can be located. The UV source is activated by a switch.

The Orasafe™ 'portable teat steriliser' is a UV device that can be attached to a feeding bottle. By turning a switch on the steriliser the UV source is activated, and automatically turns off in approximately 5 minutes after sterilisation is complete. The pacifier has a mostly transparent body.

In another pacifier steriliser product, The Ultra-Clean Pacifier Sterilizer from UV Solutions comprises a container into which the pacifier is fitted until it 'clicks into place' to close off one end of the sterilizer.

Some of the UV sterilisers of the prior art suffer from drawbacks such as the potential for the dummy or steriliser to fall or be knocked out of the device during use. Furthermore many dummy sterilisers of the prior art are not sufficiently robust to be tossed into a handbag or tote bag whilst in use.

SUMMARY OF THE INVENTION

A UV steriliser for oral appliances comprising,
(a) a base including a UV source,
(b) a lid, and
(c) an appliance holder intermediate the lid and the base adapted to hold the oral appliance adjacent to the UV source, wherein pressure exerted on the appliance holder can activate the UV source.

Typically the oral appliance is a pacifier, teat, oral prosthetic (such as a full or partial denture), mouthguard or oral orthotic (such as an orthodontic retainer). In a particularly preferred embodiment the oral appliance is a pacifier or a teat.

In a preferred embodiment, the appliance holder is adapted to hold the oral appliance by interference fit, so that the oral appliance may be manually inserted and removed. This could be achieved for example, by having a recess corresponding closely to the shape of the oral appliance or alternatively, a recess lined or bordered with soft material that elastically deforms to the shape of the oral appliance. The latter arrangement is particularly preferred because it allows oral appliances of different shapes and conformations to be located in a single appliance holder.

The lid of the UV steriliser may also be adapted to cooperate with the appliance holder and secure the oral appliance so that it is not displaced if the UV steriliser is moved. Preferably the oral appliance is held so securely in the appliance holder that the UV steriliser can, for example, be thrown into a handbag or tote bag and treated quite roughly, yet the oral appliance remains in place adjacent the UV source. Preferably the lid is hingedly attached to the base. Alternatively, the lid may be attached to the base by a screw fitting, a bayonet fitting or other convenient connection.

The UV source may be of any type known in the industry to be suitable for sterilisation of this type. The UV source typically comprises a quartz tube lamp, a copper transformer for controlling power to the lamp, a timer, a toggle switch including an on/off actuator, terminals for connection to a power source and a silicon chip for overall control of UV output. For example, a low voltage cold cathode fluorescent lamp may be suitable. The UV source may be activated and subsequently deactivated by pressure on the appliance holder, or it may automatically deactivate. The UV source may be powered by any convenient means, but preferably it is battery powered by commonly available AA or AAA size batteries to facilitate transportability.

The UV source is activated by pressure upon the oral appliance holder. In a preferred embodiment the UV source is supported on the base by biasing means and the actuator is outwardly projecting. Pressure on the appliance holder opposes the force of the biasing means so that the actuator contacts the base and is depressed, which in turn operates a switch to turn the UV source on or off. The appliance holder thus acts like a "plunger" on the activator of the UV source. Typically the pressure is manual pressure, or pressure applied by the lid when it is closed.

In a preferred embodiment of the present invention, the UV sterilisation device is generally spherical in shape, optionally including a stand so that the device can remain steady on a flat surface such as a table or shelf. In a particularly preferred embodiment, the lid is generally hemispherical in shape and of complimentary fit to a generally hemispherical shaped base. Preferably, the hemispherical lid has a peripheral edge that seals against a complementary shaped surface on the base when the lid is closed. The seal is preferably water tight, however this is not essential to the invention.

Accordingly, in a particularly preferred embodiment, the present invention is a portable UV steriliser for oral appliances comprising, (a) a generally hemispherical base including a low voltage UV source,
(b) a generally hemispherical lid having a peripheral edge adapted to form a seal with a complementary shaped surface of the base when the lid is close, and
(c) an appliance holder intermediate the lid and the base, the lid and the appliance holder cooperating to hold the oral appliance adjacent the UV source, wherein manual pressure exerted on the appliance holder can activate and deactivate the UV source.

In a particularly preferred embodiment, when the generally hemispherical lid is in the closed configuration the peripheral edge of the lid forms a seal with a complementary shaped surface of the generally hemispherical base and, overall, the UV steriliser is generally spherical in shape. Thus, the steriliser is a convenient shape to handle and push into a carrier such as a tote bag, sports bag or handbag.

The base may be of unitary construction, but typically it includes several interconnecting sub-units. Similarly the appliance holder may be of unitary construction, but typically it includes several interconnecting sub-units. The sub-units may be connected by any convenient means such as screw fitting or bayonet fitting.

The UV sterilisation device may be made of any convenient material such as polymers, preferably polymers which do not degrade rapidly when exposed to UV light. In a particularly preferred embodiment at least the lid and appliance retainer are constructed of transparent or translucent polymer.

The present invention further provides a method of sterilising an oral appliance using a UV sterilisation device according to the present invention.

DRAWINGS

Various non-limiting embodiments/aspects of the invention will now be described with reference to the following drawings in which, FIG. 1 is a drawing of a side view of one embodiment of the UV steriliser of the present invention, FIG. 2 is an exploded view of the UV steriliser of FIG. 1;

FIG. 1

Figure 1:
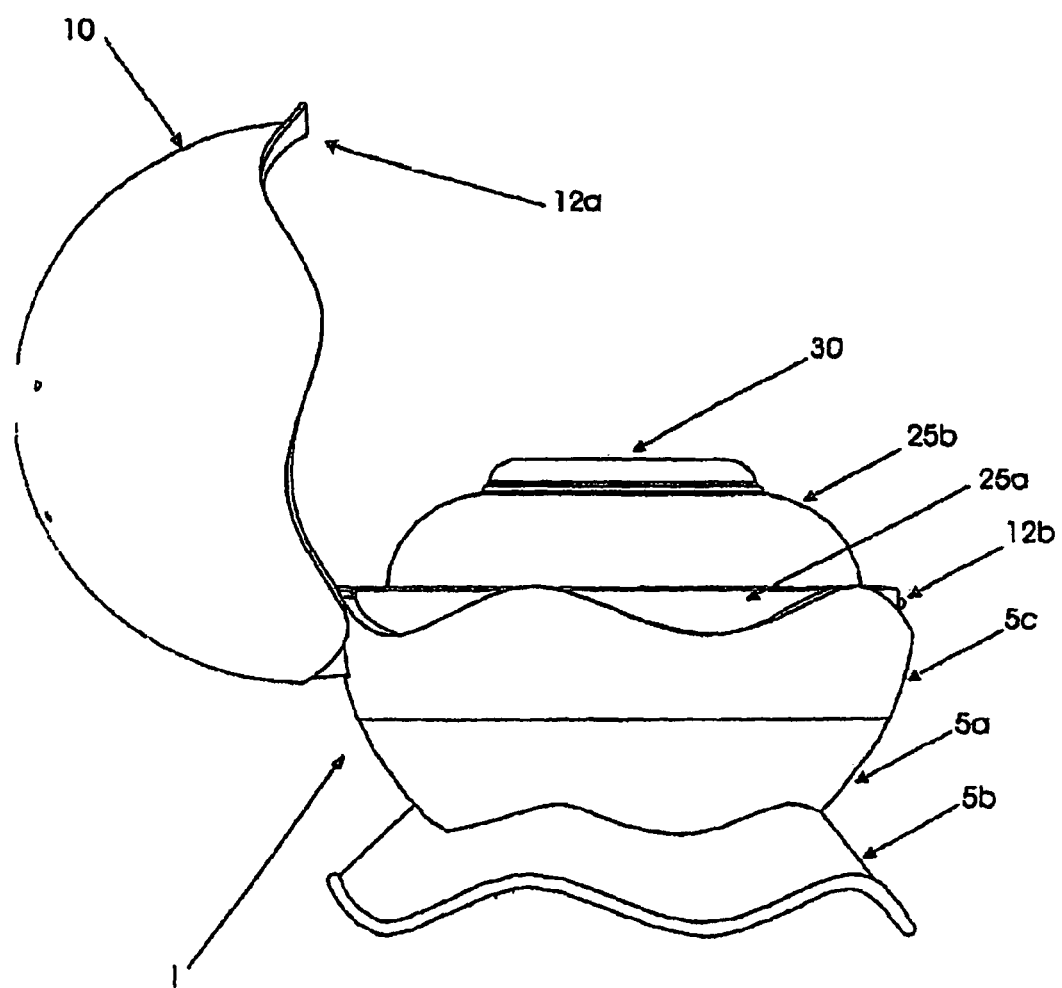

FIG. 1 is a side view of one embodiment of a UV steriliser (1) for oral appliances according to the present invention. The UV steriliser (1) includes a generally hemispherical shaped base (5) having three sub-sections—a mid-section (5a), a stand (5b) and a rim (5c). The base is adapted to enclose a UV source (not visible), and a generally hemispherical shaped hinged lid (10) with a latch (12a) that fits into a corresponding catch (12b) on the steriliser (1). In this view, the lid is open. But when the lid is in the closed configuration the base (5) and lid (10) fit together to form a generally spherical shaped UV steriliser device; the peripheral edges of the lid (10) and the rim (5c) are of complementary scalloped shapes so that they seal to form a wavelike split line horizontally around the circumference of the sphere. The base (5b) has a similar scalloped edge.

An appliance holder (25a, 25b) is located intermediate the lid (10) and the base (5), hidden from view when the lid (10) is closed. The plunger (25b) has a hollow central shaft (27) that opens at a port (30) in the top of the plunger. The lid (10) can be held closed by a latch/catch (12a,12b) combination which is located diametrically opposite a hinge about which the lid pivots.

This embodiment has the advantage that the UV steriliser has no external features such as buttons, switches, hinges, latches, screws, bolts and the like. All such features are concealed within the lid and the base. This makes the UV steriliser particularly robust with no protrusions or loose parts on the outside.

FIG. 2

Figure 2:
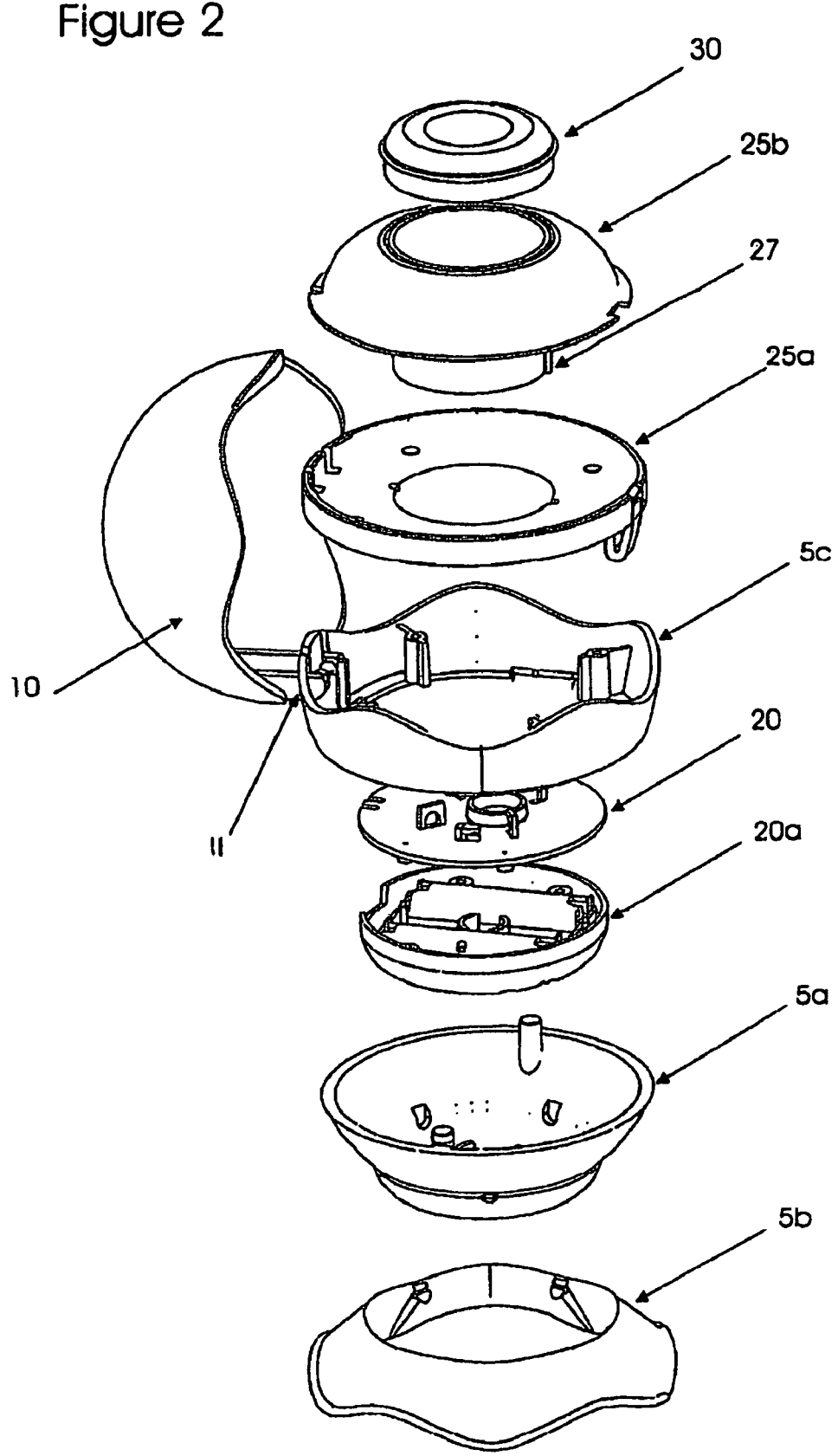

FIG. 2 is an exploded view of the UV steriliser of FIG. 1.

In this view the base mid-section (5a), stand (5b) and rim (5c) can clearly be seen, including the hinge (11) about which the lid (10) can pivot. In this view a further part of the base—the battery holder (20)—is visible. In use, the battery holder (20) is located on top of two small batteries, such as AAA batteries, and keeps them in electrical contact with the UV source (not shown). In use the UV source is located on top of the battery holder (20), with its electrical contacts projecting through recesses in the battery holder (20) to the electrical contacts on the batteries.

In this view, the appliance holder (25a, 25b) can clearly be seen. The appliance holder comprises a collar (25a) and a plunger (25b). In use the collar (25a) rests on a flange located around the perimeter of the interior surface of the base. The plunger (25b) includes a hollow central shaft (27) which in use projects through a port in the collar (25a) and contacts the UV source located on top of the battery holder (20).

The UV source is activated and deactivated by pressure upon the plunger (25b) of the oral appliance holder. In this embodiment the UV source (not shown) is supported on the top of the battery holder (20) by springs and the actuator is outwardly projecting. Manual pressure on the plunger (25b) contracts the springs so that an actuator on the UV source contacts the base and is depressed, which in turn operates a switch to turn the UV source on or off.

The hollow central shaft (27) of the plunger (25b) opens at a port (30) in the top of the plunger. The oral appliance, such as a pacifier or teat can be located in the port (30). In order to accommodate the differing sizes and conformations of pacifiers and teats, the circumference of the port supports a soft polymeric flange, so that the pacifier can be pushed into the port and held in place by interference fit with the soft flange. When closed, the lid of the UV steriliser helps to urge the pacifier or teat against the soft flange and thus ensure that it is not displaced from the appliance holder if the UV steriliser is moved.

FIG. 3

Figure 3A:
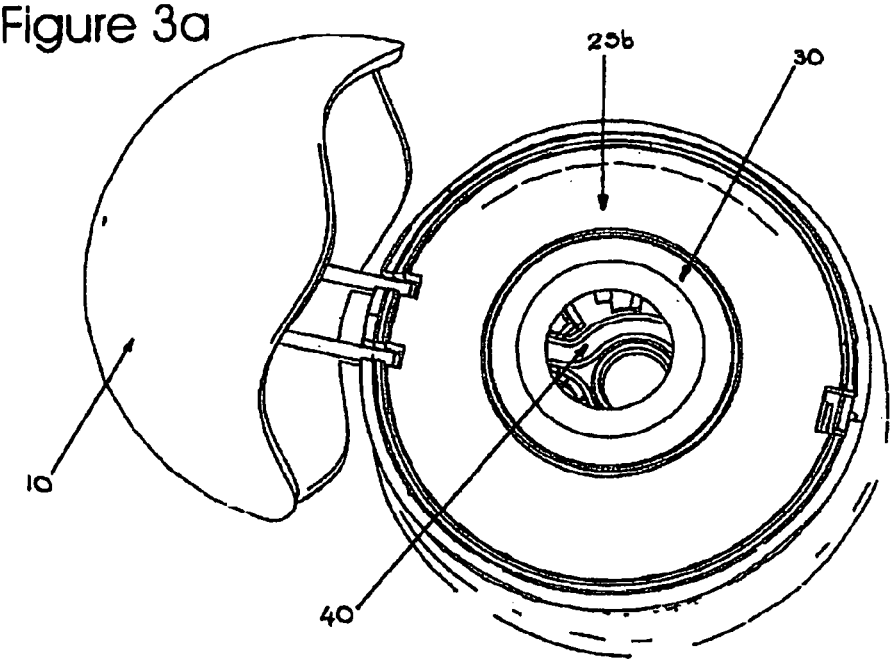
FIG. 3a is a top view and FIG. 3b is a perspective view of the base and appliance holder of the UV steriliser of FIG. 1.

FIG. 3a is a top perspective view of the UV steriliser of FIG. 1, clearly showing the lid (10), the port (30) and the plunger (25b). Through the port (30) the UV source (40) can be seen. The UV source (40) is located on top of the battery holder (20).

Figure 3B:
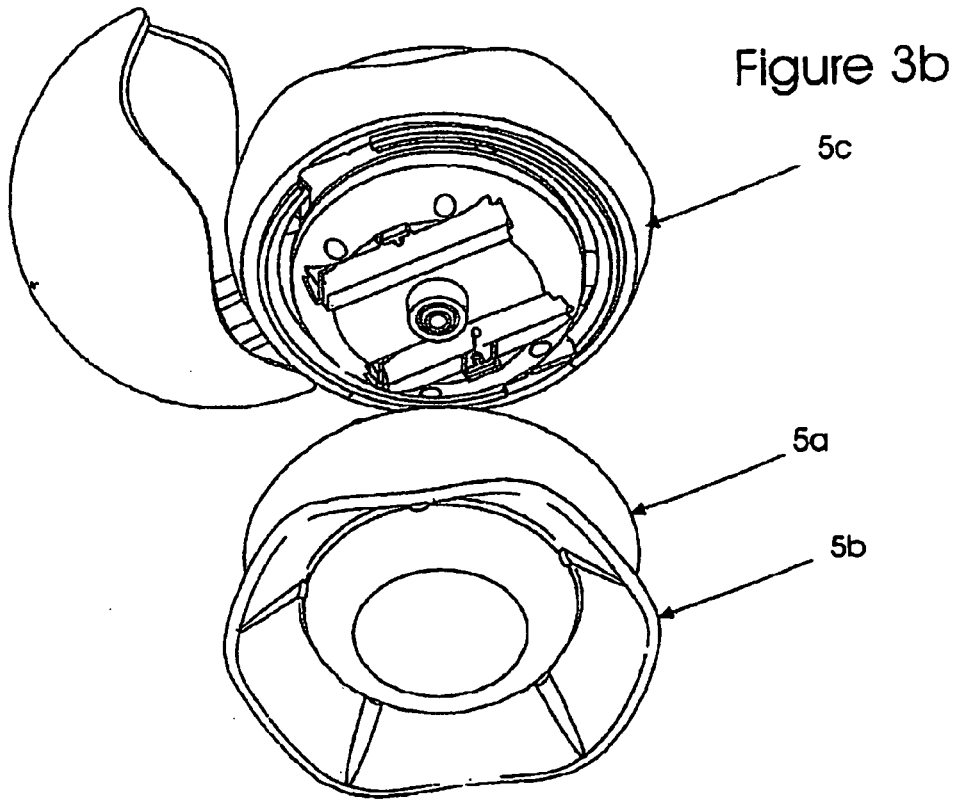

FIG. 3b is a perspective view of the base and appliance holder of the UV steriliser of FIG. 1. In this view the base mid-section (5a), stand (5b) and rim (5c) and part of the base in which the batteries may be located.

Figure 4:
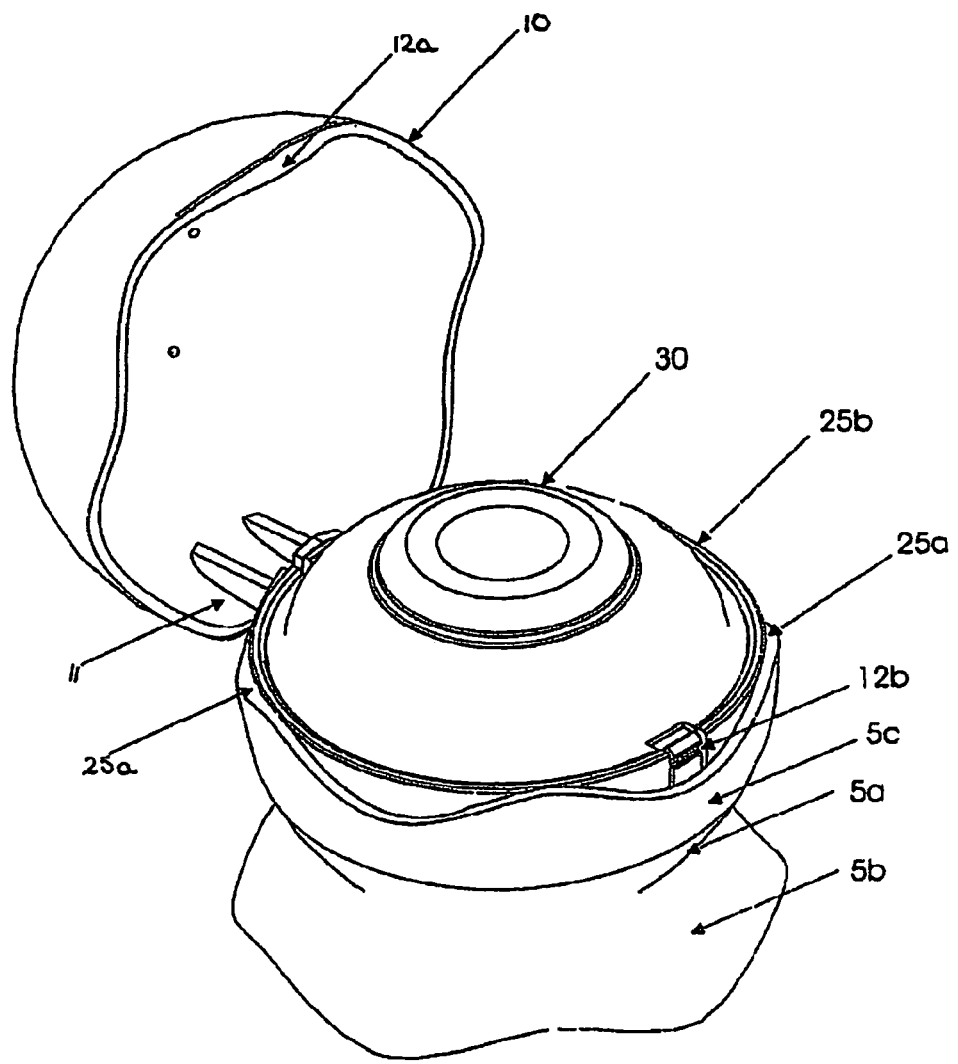
FIG. 4 is a perspective view of the UV steriliser of FIG. 1, with the lid open.

FIG. 4 is a perspective view of the UV steriliser of FIG. 1, with the lid (10) open by rotation about the hinge (11).

In this view the base mid-section (5a), stand (5b) and rim (5c) can clearly be seen. The peripheral edge of the lid (10) and the edge of the rim (5c) are of complementary (scallop) shapes and fit firmly together when the lid (10) is closed. Closure is achieved by a latch/catch (12a, 12b) provided by interference fit between the projection (12a) on the lid (10), and a catch comprising a biasing means (12b) on the collar (25a). The lid (10) moves about the hinge (11) located diametrically opposite the latch (12a,12b). The hinge (11) comprises two projections from the lid, which are received in complementary shaped recesses in the rim (5c) of the base.

FIG. 5

Figure 5:
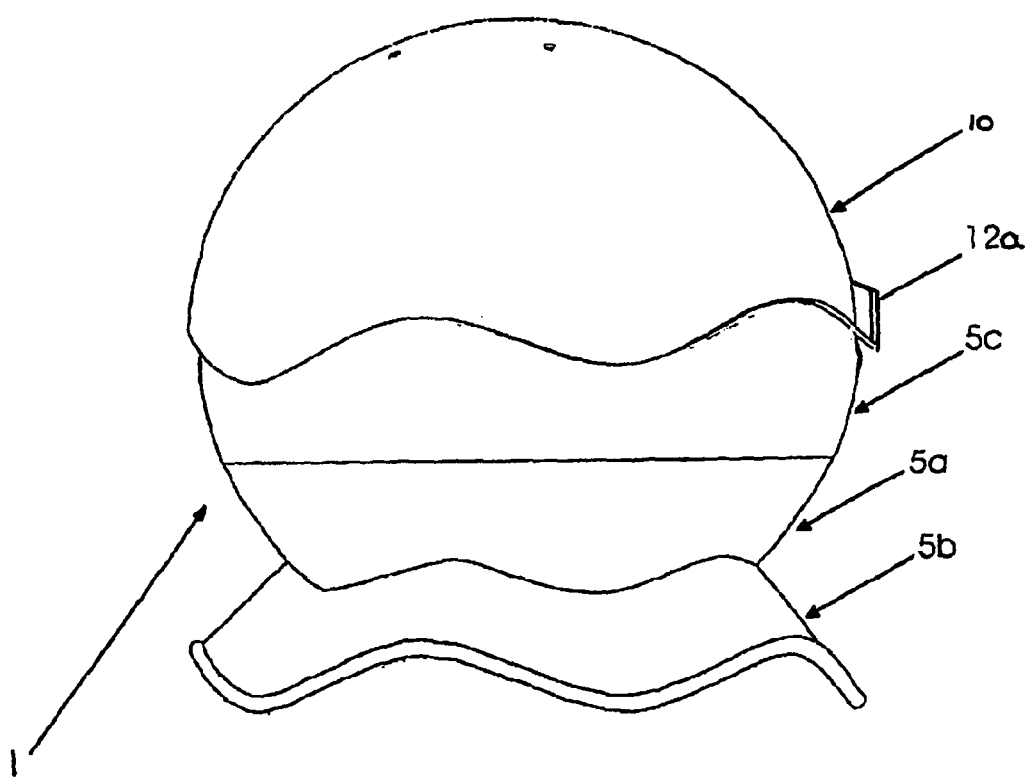
FIG. 5 is a side view of the UV steriliser of FIG. 1 with the lid closed.

FIG. 5 is a side view of the UV steriliser (1) of FIG. 1 with the lid (10) closed, the lid (10), base mid-section and rim (5a, 5c) forming a generally spherical shaped body that sits on the stand (5b) having scalloped shaped edges. The scallop shape matches the complementary shaped edges of the lid (10) and rim (5c) where they meet.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A UV steriliser for oral appliances comprising,
   (a) a generally hemispherical base including a low voltage UV source,
   (b) a generally hemispherical lid having a peripheral edge adapted to form a seal with a complementary shaped surface of the base when the lid is closed, and
   (c) an appliance holder intermediate the lid and the base the appliance, the lid and the appliance holder cooperating to hold the oral appliance adjacent the UV source,
   wherein pressure exerted on the appliance holder can activate the UV source.

2. The UV steriliser according to claim 1 wherein the appliance holder is chosen from the group comprising pacifiers, teats, oral prosthetics, mouthguards and oral orthotics.

3. The UV steriliser according to claim 1 wherein pressure exerted on the appliance holder can be used to activate and subsequently deactivate the UV source.

4. The UV steriliser according to claim 1 wherein the UV source deactivates automatically.

5. The UV steriliser according to claim 1 wherein pressure can be exerted on the appliance holder manually, or by closing the lid.

6. The UV steriliser according to claim 1 wherein the appliance holder is adapted to hold the oral appliance by interference fit.

7. A UV steriliser according to claim 1 wherein when the lid is in the closed position the peripheral edge of the lid forms a seal with a complementary shaped surface of the base and the UV steriliser is generally spherical in shape.

8. The UV steriliser according to claim 1 wherein the base comprises a stand, a mid-section, and a rim.

9. A UV steriliser according to claim 8 wherein any one or more of the lid, stand, mid-section and rim are removably connected.

10. A method of sterilising an oral appliance using the UV steriliser according to claim 1, comprising the steps of,
    (a) locating an oral appliance in the appliance holder, and
    (b) exerting pressure on the appliance holder to activate the UV source, and
    (c) subjecting the oral appliance to UV radiation from the UV source for a period of time.

11. A method of sterilising an oral appliance using a UV steriliser for oral appliances comprising,
    (a) a base including a UV source,
    (b) a lid, and
    (c) an appliance holder intermediate the lid and the base, the appliance holder being adapted to hold the oral appliance adjacent the UV source,
    wherein pressure exerted on the appliance holder can activate the UV source, and comprising the steps of:
    comprising the steps of,
    (a) locating an oral appliance in the appliance holder, and
    (b) exerting pressure on the appliance holder to activate the UV source, and
    (c) subjecting the oral appliance to UV radiation from the UV source for a period of time.

* * * * *